United States Patent
Giron et al.

(10) Patent No.: US 8,485,984 B2
(45) Date of Patent: Jul. 16, 2013

(54) PORTABLE BREATH COLLECTION SYSTEM FOR USE IN BREATH TESTS

(75) Inventors: Boaz Giron, Jerusalem (IL); Julian Daich, Jerusalem (IL); Ilan Ben-Oren, Jerusalem (IL)

(73) Assignee: Exalenz Bioscience Ltd., Modiin (IL)

(*) Notice: Subject to any disclaimer, the term of this patent is extended or adjusted under 35 U.S.C. 154(b) by 922 days.

(21) Appl. No.: 10/506,872

(22) PCT Filed: Mar. 3, 2003

(86) PCT No.: PCT/IL03/00162
§ 371 (c)(1),
(2), (4) Date: Apr. 25, 2005

(87) PCT Pub. No.: WO03/073935
PCT Pub. Date: Sep. 12, 2003

(65) Prior Publication Data
US 2005/0177056 A1    Aug. 11, 2005

(30) Foreign Application Priority Data
Mar. 3, 2002 (IL) .......................................... 148468

(51) Int. Cl.
*A61B 5/08* (2006.01)
(52) U.S. Cl.
USPC ........................................ 600/543; 600/529
(58) Field of Classification Search
USPC .................. 600/543, 532; 422/84; 73/23.2
See application file for complete search history.

(56) References Cited

U.S. PATENT DOCUMENTS
4,390,483 A    6/1983    Willems et al.
4,448,058 A    5/1984    Jaffe et al.
(Continued)

FOREIGN PATENT DOCUMENTS
EP    1062909 A2    12/2000
EP    1 205 750 A2    5/2002
(Continued)

OTHER PUBLICATIONS

Cornetta, Angelyn M., et al., "Use of a [$^{13}$C]urea breath test for detection of gastric infection with *Helicobacter* spp in dogs", American J. Veterinary Res., USA, Nov. 1998, vol. 59, No. 11, p. 1364-1369.

(Continued)

*Primary Examiner* — Patricia Mallari
*Assistant Examiner* — Christian Jang
(74) *Attorney, Agent, or Firm* — Rodney J. Fuller; Booth Udall Fuller, PLC (57) ABSTRACT

An automatic breath collecting and sampling system, which is preferably carried by the subject, or otherwise kept with him or near him, for the recommended duration of the collection period. The system collects samples in separate switchable containers, either at predetermined time intervals, or in response to an automatic stimulus, which could be related to the breath content itself, or to another physiological signal, such as the subject s pulse rate, breath rate, blood pressure, or temperature, or in response to a signal related to an environmental effect, such as the presence of a strong concentration in the air of a foreign gas, which could be detected by an electrochemical sensor, or manually by the subject after being prompted by the system. After collection of the requisite number of separate containers, they may be detached and sent for analysis or other treatment.

15 Claims, 6 Drawing Sheets

U.S. PATENT DOCUMENTS

| | | | |
|---|---|---|---|
| 4,490,482 | A | 12/1984 | Mathieu |
| 4,639,432 | A | 1/1987 | Holt et al. |
| 4,680,956 | A | 7/1987 | Huszczuk |
| 4,684,805 | A | 8/1987 | Lee et al. |
| 4,723,435 | A | 2/1988 | Huszczuk |
| 4,756,000 | A | 7/1988 | Macken |
| 4,757,512 | A | 7/1988 | Macken |
| 4,909,259 | A | 3/1990 | Tehrani et al. |
| RE33,493 | E | 12/1990 | Lee et al. |
| 5,005,571 | A * | 4/1991 | Dietz ............. 128/205.25 |
| 5,042,501 | A * | 8/1991 | Kenny et al. .............. 600/532 |
| 5,069,220 | A * | 12/1991 | Casparie et al. ............. 600/532 |
| 5,140,993 | A * | 8/1992 | Opekun et al. .............. 600/543 |
| 5,146,294 | A | 9/1992 | Grisar et al. |
| 5,159,934 | A * | 11/1992 | Hoberman ............... 600/532 |
| 5,179,958 | A * | 1/1993 | Mault .................. 600/531 |
| 5,300,859 | A | 4/1994 | Yatsiv et al. |
| 5,317,156 | A | 5/1994 | Cooper et al. |
| 5,394,236 | A | 2/1995 | Murnick |
| 5,479,019 | A | 12/1995 | Gross |
| 5,486,699 | A | 1/1996 | Fabinski et al. |
| 5,501,231 | A | 3/1996 | Kaish |
| 5,533,513 | A * | 7/1996 | Ueda et al. .............. 600/543 |
| 5,543,621 | A | 8/1996 | Sauke et al. |
| 5,640,014 | A | 6/1997 | Sauke et al. |
| 5,657,750 | A | 8/1997 | Colman et al. |
| 5,711,306 | A * | 1/1998 | Guilluy ................. 600/543 |
| 5,747,809 | A | 5/1998 | Eckstrom |
| 5,787,885 | A * | 8/1998 | Lemelson ............... 600/309 |
| 5,818,580 | A | 10/1998 | Murnick |
| 5,908,789 | A | 6/1999 | Weckstrom |
| 5,944,670 | A | 8/1999 | Katzman |
| 5,957,858 | A | 9/1999 | Micheels et al. |
| 5,961,470 | A | 10/1999 | Wagner et al. |
| 5,962,335 | A | 10/1999 | Katzman |
| 5,964,712 | A | 10/1999 | Kubo et al. |
| 6,067,989 | A | 5/2000 | Katzman |
| 6,096,558 | A | 8/2000 | Stock |
| 6,099,481 | A * | 8/2000 | Daniels et al. ............. 600/538 |
| 6,106,479 | A | 8/2000 | Wunderlich et al. |
| 6,186,958 | B1 | 2/2001 | Katzman et al. |
| 6,437,316 | B1 | 8/2002 | Colman et al. |
| 6,488,635 | B1 * | 12/2002 | Mottram ................. 600/551 |
| 6,656,127 | B1 * | 12/2003 | Ben-Oren et al. ........... 600/532 |
| 2003/0050567 | A1 * | 3/2003 | Baghdassarian ............ 600/532 |

FOREIGN PATENT DOCUMENTS

| | | |
|---|---|---|
| GB | 2 324 387 A1 | 10/1998 |
| WO | WO-98/30888 A1 | 7/1998 |
| WO | WO-99/14576 | 3/1999 |
| WO | WO-00/67634 | 11/2000 |
| WO | WO 00/67634 | 11/2000 |

OTHER PUBLICATIONS

Schommartz, B., et al., "Significance of Diagnostic Parameters in [$^{13}$C]Octanoic Acid Gastric Emptying Breath Tests" Isotopes Environ. Health Stud., NL, 1998, vol. 34, No. 1-2, pp. 135-143.

Shreeve, Walton W., et al., "Test for Alcoholic Cirrhosis by Conversion of [$^{14}$C]—or [$^{13}$C]Galactose to Expired $CO_2$", Gastroenterology, Jul. 1976, vol. 71, No. 1, pp. 98-101.

Lotterer, E., et al., "The simplified $^{13}$C-urea breath test—One point analysis for detection of *Helicobacter pylori* infection", Z. Gastroenterol., 1991, vol. 29, pp. 590-594.

Cheng, Wu-Hsun, et al., "Technology development in breath microanalysis for clinical diagnosis", J. Lab. Clin. Med., Mar. 1999, vol. 133, No. 3, pp. 218-228.

Pleil, J. D., et al., "Collection of a single alveolar exhaled breath for volatile organic compounds analysis", American Journal of Industrial Medicine, 1995, vol. 28, pp. 109-121.

Spanel, Patrik, et al., "Influence of water vapour on selected ion flow tube mass spectrometric analyses of trace gases in humid air and breath", Rapid Communications in Mass Spectrometry, 2000, vol. 14, pp. 1898-1906.

Pleil, Joachim D., et al., "Measurement of volatile organic compounds in exhaled breath as collected in evacuated electropolished canisters", Journal of Chromatography B, 1995, vol. 665, pp. 271-279.

Schubert, Jochen K., et al., "$CO_2$-controlled sampling of alveolar gas in mechanically ventilated patients", J. Appl. Physiol., 2001, vol. 90, pp. 486-492.

Narasimhan, L. R., et al., "Correlation of breath ammonia with blood urea nitrogen and creatinine during hemodialysis", PNAS, Apr. 10, 2001, vol. 98, No. 8, pp. 4617-4621.

Dunn, C. D. R., et al., "Ammonia vapour in the mouth as a diagnostic marker for *Helicobacter pyloi* infection: preliminary 'proof of principle' pharmacological investigations", British Journal of Biomedical Science, 2001, vol. 58, pp. 66-75.

International Search Report for PCT/IL03/00162 dated Oct. 5, 2005.

Roecker, K. et al., "First-pass effect of an intravenous bolus of [$^{13}$C]bicarbonate displayed breath-by-breath", *J Appl Physiol*, 90:2181-2187 (2001).

Phillips, Michael, "Method for the Collection and Assay of Volatile Organic Compounds in Breath", *Analytical Biochemistry*, 247:272-278 (1997).

Urita, Y. et al., "Breath sample collection through the nostril reduces false-positive results of $^{13}$C-urea breath test for the diagnosis of *Helicobacter pylori* infection", *Digestive and Liver Disease*, 36:661-665 (2004).

Declaration of Ilan Ben-Oren Under 37 C.F.R. § 1.132 dated Dec. 23, 2010, pp. 1-12.

Excerpt from INFAI.com website regarding "*13*C-Octanoic acid breath test to determine gastric emptying rate". [online] [retrieved on Jan. 5, 2011]. Retrieved from the Internet: <URL: http://www.infai.com/innovations/gastromotal.php>.

Excerpt from Menssana Research website regarding "BCA 5.0 User's Guide". [online] [retrieved on Nov. 19, 2011]. Retrieved from the Internet: <URL: http://www.menssanaresearch.com/bcaguide_5.htmp>.

Counterpart European Patent No. 1480557 Office Action dated Jul. 10, 2007.

* cited by examiner

PORTABLE BREATH COLLECTION SYSTEM FOR USE IN BREATH TESTS

This is a U.S. national phase application under 35 U.S.C. §371 of International Patent Application No. PCT/IL03/00162, filed Mar. 3, 2003, and claims the benefit of Israeli Patent Application No. 148468 filed Mar. 3, 2002.

FIELD OF THE INVENTION

The present invention relates to the field of breath tests and methods of collecting the breath samples for remote analysis, and especially for use in breath tests which take a long time to complete or require special treatment of the sampled gases.

BACKGROUND OF THE INVENTION

A number of breath tests are known for use in diagnosing various clinical conditions in subjects. Many of these breath tests are comparatively quick, and give definitive results within a matter of a few minutes or at most, tens of minutes. When a real-time breath tester is used, such as the Breath ID™ supplied by Oridion Medical Ltd., of Jerusalem, Israel, such quick breath tests are generally performed by keeping the subject connected to the breath tester, and sampling breaths directly into the breath tester at predetermined intervals, until the result is determined. If an off-line breath analyzer is used, such breath tests are generally performed by collecting breaths at predetermined intervals in bags, and transferring them for later analysis to the off-line breath analyzer. Such off-line breath tests inevitably mandate a longer test period since the ongoing result of the test is not known in real time, and samples should generally be collected until it is certain that a definitive result is obtained.

Some breath tests however, such as that for determining orocaecal transit time (OCTT), require a long time to complete the sampling process necessary to achieve a definitive result, and can last for up to approximately 6 hours. This may be problematic for a number of reasons. Other breath tests require special collection conditions, which are not generally met by currently used breath test procedures, whether on-line tests, or tests using analysis at a remote location.

Some of the above-mentioned problems can be summarized as follows:

(i) Subject inconvenience of being connected to a breath testing instrument for such a long time;
(ii) Poor utilization of the breath test instrument, which is generally an expensive piece of equipment, and it is not cost-effective for a single subject to monopolize a breath test instrument for several hours;
(iii) In cases wherein breath samples have to be collected and sent to a laboratory, it causes staff inconvenience in dealing with very large number of samples, both in ensuring that the samples are taken, and at the correct times;
(iv) In cases wherein breath samples have to be collected and sent to a remote laboratory, differences in the $CO_2$ content between the breath samples may introduce systematic errors in isotopic $CO_2$ measurement. Such changes may arise especially if the samples are manually taken without the use of a concentration regulating mechanism during the collection procedure, or if the subject to be analyzed does not exhale in a steady state condition throughout the test. Similar errors may also occur in other isotopically labeled breath samples.
(v) Some breath tests require an absolute knowledge of the volume of exhaled $CO_2$ throughout the test, in addition to the isotope concentration of the species of carbon dioxide detected. Some examples of such breath tests are those for determining liver function or pancreatic function, in which the breath test analyzes exhaled products resulting from metabolic pathways through the organ being tested. For such tests, the conventional methods of assuming a constant volume according to the weight and height of the patient, according to the known Body Surface Area (BSA) parameter calculation may not be accurate due to physiological factors unrelated to the measurement In other breath tests, it is not the absolute volume that is required, but the change in absolute volume as the test proceeds. Since the volume is not necessarily directly related to the isotope concentration measured by the breath test, prior art breath tests do not always provide accurate results for such tests.
(vi) Some breath analysis procedures, such as those utilized in the analysis of volatile organic compounds (VOC), need special procedures for collecting and preparing the samples to prevent undesired sources of error. Such errors could arise from the presence of VOC's in the ambient gases, from the differences in normal metabolism rates between individuals, and from the presence of undesired factors affecting the samples, such as humidity. Current collection procedures do not generally fulfil these requirements.

There therefore exists an important need for a breath collection apparatus, particularly for use with breath tests which extend over long periods, which will overcome some of the above-mentioned disadvantages of present breath testing sample collection procedures.

The disclosures of all publications mentioned in this specification, are hereby incorporated by reference, each in its entirety.

SUMMARY OF THE INVENTION

The present invention seeks to provide a new breath collection system which obviates the need for the subject to remain attached to or close to a breath tester in the case of an on-line breath test, or close to a breath collection point in the hospital or clinic for off-line breath analysis procedures.

There is thus provided in accordance with a preferred embodiment of the present invention, an automatic, portable, breath sampling system, which is preferably carried by the subject, or otherwise kept with him or near him, for the recommended duration of the test. According to one preferred embodiment, the system collects samples at predetermined time intervals. According to another preferred embodiment, the system collects samples in response to an automatic stimulus, which could be related to the breath content itself, or to another physiological signal, such as the subject's pulse rate, breath rate, blood pressure, or temperature. According to another preferred embodiment of the invention, preferably used to determine the effects of environmental hazards or pollution, the system collects samples in response to a signal related to an environmental effect, such as the presence of a strong concentration in the air of a foreign gas, which could be detected by an electrochemical sensor.

If the prompting signal for sample collection is based on the breath content itself, that prompt may preferably be obtained from the output of a capnographic analyzer at the input to the collection system. The capnograph should preferably identify the sample as a breath sample before the commencement of collection, and should provide input signals to the gas collection system at the predetermined $CO_2$ level above which breath is to be collected. If another physiological signal is used to prompt breath collection, then an appropriate sensor must be provided, and its output interfaced with the breath collection system control.

According to another preferred embodiment of the present invention, the pneumatics and plumbing system used to collect the breath samples may be similar to those used in the intermediate chamber embodiments, described in the co-pending PCT application, International Publication No. WO 99/14576 for "Isotopic Gas Analyzer", hereby incorporate by reference in its entirety, whereby only a predetermined part of each relevant breath is collected. The part of the relevant breath collected is generally determined by a capnographic probe at the entrance of the system, which analyses the input breath waveform in real time. The whole collection procedure is preferably under control of a central controller.

According to another preferred embodiment of the present invention the capnograph output could be used to identify and differentiate alveolar breath, which has taken part in pulmonary gas exchange, from air originated from the subject's respiratory dead space or from the environmental air. This may also thus allow collection of air from the environment, or from the dead space when of interest. Thus, for instance, air from the environment would be sampled from the baseline region of the waveform, which is the inspiratory region where virtually none of the subject's pulmonary exhaled breath is mixed in. Air from the subject's dead space would be sampled from the rising part of the waveform, where the exhaled pulmonary air pushes out the dead space air, which is air from the subject's mouth, trachea and bronchial tubes, which did not originate from the lungs themselves. Alveolar breath would be collected from the plateau of the waveform. In general, throughout this application, and as claimed, use of the term "breath" is generally understood to mean the exhaled breath of the subject, except in those embodiments where it refers to inhaled breath or dead space breath, as generally sampled by a nasal or an oral/nasal cannula, or an airway adaptor.

According to more preferred embodiments of the present invention, the rate of collection may be made dependent on a characteristic of the breath being measured at the input. Thus, collection rate could preferably be increased when changes of relevance are detected in the characteristic of the breath being measured, e.g. if the carbon dioxide concentration changes significantly, or in any of the other parameters being monitored in the subject or in the ambient.

According to another preferred embodiment of the present invention the collection system can includes means to monitor the heart rate throughout the collection procedure, to allow the monitoring of changes in a metabolism rate of the subject that in particular, cause changes in the volume of carbon dioxide exhalation. As is known, the heart rate is one of the indicators of the overall metabolic rate of a subject Blood pressure may also be used. According to another preferred embodiment the $CO_2$ waveform is continuously analyzed to evaluate changes in the rate of carbon dioxide exhalation throughout the collection period.

Analysis of volatile organic compounds (VOC) is commonly performed using mass spectrometry and gas chromatography after collection and preparation of the samples. One recent prior art device for the measurement of VOC's is disclosed in the European Patent Application EP1205750A2 to Amirav. Alternatively, use is made of sensors based on the measurement of temperature, pressure and viscosity of a gas at a given volume such as a microchip gas analyzer; or optical spectrometers such as those based on Raman spectrometry, cavity ring resonance spectrometry or non dispersive infra red spectrometry. For the measurement of VOC levels in the breath, additional requirements prior to the gas analysis must be considered, because of the very small levels to be detected, typically of the order of microgram per liter concentrations, or even less. Some examples of such VOC breath tests are to detect the presence of acetone, which is present in the breath of some types of diabetic patients, or alcohol, or carbon monoxide, and others, as described, for instance in the articles entitled "Collection of Single Alveolar Exhaled Breath for Volatile Organic Compound Analysis" by J. D. Pleil et al., published in American Journal of Industrial Medicine, Vol. 28, pp. 109-121 (1995), and "Technological Development in Breath Microanalysis for Clinical Diagnosis" by Wu-Hsun Cheng et al., in Journal of Laboratory Clinical Medicine, Vol. 133, pp. 218-228 (1999). The VOC detected in human alveolar breath may come from products of metabolism, which is the level being sought in the breath test, or it may come from inhaled ambient air, in which case the level is simply an indicator of the gas abundance in the background, and is of secondary interest. For this reason, it is generally necessary always to determinate the level of VOC in human expired air in comparison with background VOC levels.

Alternatively in some breath tests, such as the ammonia breath test for the detection of *Helicobacter pylori*, breath samples must be obtained from the body's dead space and not from the alveolar gas. Most of the ammonia generated in this test comes directly from the stomach and not by metabolic paths which result in its presence in exhaled breath from the lungs.

Different methods and apparatus have been proposed to overcome the above-mentioned difficulties. One such method, for the performance of VOC breath tests, is the respiration of very pure air before the sampling. This, however, requires long preparation, is time consuming, unpractical for sequential measurement and requires a large volume of highly purified air, which is an expensive product. Alternatively, manually activated valves or simple pressure valves are used to attempt to isolate exhaled alveolar samples from other sources of gas, but these methods are inaccurate and unpractical for collecting gas from the inhaled air. For collecting dead space gases, catheters and aspiring devices have been proposed, but such devices are invasive, and may be inaccurate and impractical.

In order to solve the above mentioned problems, there is provided a system according to another preferred embodiment of the present invention, that accurately collects alveolar gas, environmental or dead space gas based on the carbon dioxide waveform information provided by a capnographic probe. This allows the VOC levels in the alveolar breath to be compared to ambient or dead space levels thus ensuring an accurate measurement. Alternatively a fast oxygen probe could replace the capnographic probe for similar purposes. In this case, a lower level of oxygen than the ambience level characterizes alveolar gas from breath.

Although the invention is described in this application for use with breath tests, it is to be understood that it is not meant to be limited to this such tests but may be advantageously used for collecting breath samples for any other long term clinical tests or trials which require samples of breath.

In accordance with yet another preferred embodiment of the present invention, there is provided a system for collecting a plurality of samples of breath from a subject, comprising a breath conduit for conveying breath from the subject to the system, a plurality of sample containers for collection of the plurality of samples, a controller, and a sample distributor which directs different predetermined samples of the breath to different ones of the plurality of sample containers according to the controller.

In the above mentioned system, the controller may preferably cause the sample distributor to direct the samples at predetermined times, which may preferably be at fixed time intervals, or may preferably be determined by a characteristic of the breaths of the subject. This characteristic of the breaths may preferably be at least one of the carbon dioxide concentration, the oxygen concentration, the excess pressure, the temperature, the humidity, the flow rate and the sound of the breaths.

Alternatively and preferably, the predetermined times may be determined by at least one physiological characteristic of the subject, which could be any one or more of the subject's breath composition, breath rate, heart rate, blood pressure, gastric pH value and temperature, or any other suitable characteristic.

Alternatively and preferably, the predetermined times may be determined by an output from one or more of an implanted medical device, such as a drug delivery system, an ingested medical device, such as an endoscopic capsule, and an endoscopic medical device.

Furthermore, in any of the above-mentioned embodiments, the breath conduit may comprise a nasal or an oral/nasal cannula, or a breath tube.

There is further provided in accordance with yet another preferred embodiment of the present invention, a system for collecting a plurality of samples of breath from a subject, comprising a breath conduit for conveying breath from the subject to the system, a breath analyzer for determining a characteristic of the breath, a valving system to collect at least part of the breath, the valving system being actuated according to the characteristic of the breath, a plurality of sample containers for collection of the plurality of samples, and a sample distributor for directing different predetermined samples of the at least part of the breath to different ones of the plurality of sample containers. The sample distributor may preferably be operated manually. Alternatively and preferably, the system may also comprise a controller operative to cause the sample distributor to direct the different predetermined samples to the different ones of the plurality of sample containers.

In the above mentioned systems, the breath analyzer may preferably be a capnographic analyzer, and the characteristic is then the carbon dioxide concentration of the breath. In such a case, the above-mentioned part of the breath is determined by the carbon dioxide concentration of the breath. According to more preferred embodiments, the part of the breath may be collected when the carbon dioxide concentration of the breath is at the plateau value of its waveform, such that alveolar air is sampled, or it may be collected when the carbon dioxide concentration of the breath is at the rising part of its waveform, such that dead space air is sampled, or it may be collected when the carbon dioxide concentration of the breath is at the baseline of its waveform, such that inhaled air is sampled.

The above-mentioned system may also comprise a gas volume controller such that equal volumes may be collected in said containers, and wherein at least a first and a second of the sample containers contain a material which absorbs a predetermined gas of the breath of the subject, and wherein the controller is adapted to direct breath exhaled when its carbon dioxide concentration is at the plateau value of its waveform into a first of said sample containers, and breath when the carbon dioxide concentration of the breath is at the baseline of its waveform into a second of the sample containers, such that the system can determine the ratio of the concentration of the predetermined gas by the subject to that contained in ambient air. At least the first and second of the plurality of sample containers preferably comprises a heater for expelling the predetermined gas of the breath of the subject. Also, the volume controller may comprise a flow meter for measuring the volumes of breath into the sample containers, in conjunction with the controller, which ensures equal volume collection. Alternatively, the volume controller may comprise an intermediate chamber system for so ensuring. The above described embodiments enable the system to be used for VOC analysis, where the predetermined gas contains volatile organic compounds.

Alternatively and preferably, the above mentioned breath analyzer may be an oxygen content analyzer, and the characteristic is then the oxygen concentration of the breath.

In the last mentioned systems, the controller may preferably cause the sample distributor to direct the samples at predetermined times, which may preferably be at fixed time intervals, or may preferably be determined by a characteristic of the breaths of the subject. This characteristic of the breaths may preferably be at least one of the carbon dioxide concentration, the oxygen concentration, the excess pressure, the temperature, the humidity, the flow rate and the sound of the breaths.

Alternatively and preferably, the predetermined times may be determined by at least one physiological characteristic of the subject, which could be the subject's breath composition, breath rate, heart rate, blood pressure, gastric pH value or temperature, or any other suitable characteristic.

Alternatively and preferably, the predetermined times may be determined by an output from one or more of an implanted medical device, such as a drug delivery system, an ingested medical device, such as an endoscopic capsule, and an endoscopic medical device.

In accordance with still another preferred embodiment of the present invention, there is provided a system for collecting a plurality of samples of breath from a subject, comprising a breath conduit for conveying breath from the subject to the system, a valving system to collect at least part of the breath, the valving system being actuated according to a physiological characteristic of the subject, a plurality of sample containers for collection of the plurality of samples, and a sample distributor for directing different predetermined samples of the at least part of the breath to different ones of the plurality of sample containers. The at least one physiological characteristic of the subject may preferably be any one or more of the subject's breath composition, breath rate, heart rate, blood pressure, gastric pH value, temperature, or any other suitable characteristic. Furthermore, the breath conduit may preferably comprise a nasal or an oral/nasal cannula, or a breath tube.

There is further provided in accordance with still another preferred embodiment of the present invention, a system for collecting a plurality of samples of breath from a subject, comprising a breath tube through which the subject provides breath by blowing, a pressure sensor for determining the pressure of the breath, a valving system for collecting at least one sample from at least part of the breath, the valving system being actuated according to the pressure of the breath, a plurality of sample containers for collection of the plurality of samples, and a sample distributor for directing different predetermined samples of the at least part of the breath to different ones of the plurality of sample containers.

The sample distributor may preferably be operated manually. Alternatively and preferably, the system may also comprise a controller operative to cause the sample distributor to direct the different predetermined samples to the different ones of the plurality of sample containers. If the system includes a controller, the controller may preferably prompt the subject at predetermined times to provide breath by blowing. These predetermined times may be fixed time intervals, or they may be determined by a physiological characteristic of the subject, which could be any one or more of the subject's breath composition, breath rate, heart rate, blood pressure, gastric pH value or temperature, or any other suitable characteristic. Alternatively and preferably, the predetermined times may be determined by an output from one or more of an implanted medical device, such as a drug delivery system, an ingested medical device, such as an endoscopic capsule, and an endoscopic medical device.

In accordance with yet a further preferred embodiment of the present invention, there is also provided a system for collecting a plurality of samples of breath from a subject, comprising a breath tube through which the subject provides breath by blowing, a plurality of sample containers for collection of the plurality of samples, a one way check valve for directing the breath samples from the breath tube to the plurality of sample containers, and a sample distributor for directing different predetermined samples of the breath to different ones of the plurality of sample containers.

The sample distributor may preferably be operated manually. Alternatively and preferably, the system may also comprise a controller operative to cause the sample distributor to direct the different predetermined samples to the different ones of the plurality of sample containers. If the system includes a controller, the controller may preferably prompt the subject at predetermined times to provide breath by blowing. These predetermined times may be fixed time intervals, or they may be determined by a physiological characteristic of the subject, which could be any one or more of the subject's breath composition, breath rate, heart rate, blood pressure, gastric pH value or temperature, or any other suitable characteristic. Alternatively and preferably, the predetermined times may be determined by an output from one or more of an implanted medical device, such as a drug delivery system, an ingested medical device, such as an endoscopic capsule, and an endoscopic medical device.

There is also provided in accordance with yet a further preferred embodiment of the present invention, a method and a breath collection apparatus for collecting breath samples such that they are in a suitable form for determining the concentration of volatile organic compound in breath of a subject relative to the ambient. The apparatus comprises:
(i) a breath collection device which collects in a first container a first sample obtained from the subject's breath indicative of the ambient air inhaled by the subject, and
(ii) a second container in which the breath collection device collects a second sample of alveolar air in the breath of the subject.

The breath is preferably analyzed by means of a capnographic probe, whereby the first sample is collected at the baseline of the waveform of the breath of the subject, and thus is representative of inhaled air from the ambient, and the second sample is collected from the plateau volume of the breath of the subject, and thus is representative of the exhaled gas from the subject.

There is also provided in accordance with another preferred embodiment of the present invention, a system for determining the concentration of VOC in the breath of a subject, which utilizes the above-mentioned breath collection apparatus, and in which the first and second samples are passed by means of a gas transfer system to be analyzed for the concentrations of the volatile organic compound, for example by means of a gas analyzer as described in the prior art. The concentration of the volatile organic compound in the first sample is compared to that in the second sample.

There is even further provided in accordance with another preferred embodiment of the present invention, a method of determining in a breath test of a subject, the volume of a species in the subject's breath over a period of interest, comprising the steps of:
(i) providing a breath test apparatus comprising a probe at its input, such that the concentration of the species in the breath of the subject is continuously monitored,
(ii) measuring the breathed volume rate of the species in the subject's breath as a function of the integrated concentration of the species, such that the relationship of breathed volume to measured concentration is known,
(iii) integrating over the period of interest, the total concentration of the species determined by the probe, and
(iv) converting the integrated concentration of the species to the absolute volume of the species by means of the relationship.

Furthermore, in accordance with yet another preferred embodiment of the present invention, there is provided a method of determining, in a breath test of a subject, the change in volume of a species in the subject's breath, comprising the steps of:
(i) measuring a first concentration of the species in the breath of the subject by means of the breath test,
(ii) measuring a second concentration of the species in the breath of the subject by means of the breath test,
(iii) monitoring a physiological parameter of the subject related to the metabolic rate of the subject, for change in the parameter between the measuring of the first concentration and the second concentration, and
(iv) adjusting the second concentration according to change determined in the physiological parameter, such that the second concentration measured is representative of the volume of the species in the subject's breath.

In the above-mentioned method, the physiological parameter of the subject may preferably be at least one of the pulse rate of the subject, the integrated area under a capnographic measurement of the subject's breath, and the breath flow rate of the subject.

There is also provided in accordance with a further preferred embodiment of the present invention, a system according to any of the above-described embodiments and in which the sample containers contain a material which absorbs at least part of the breath of the subject. In such embodiments, the material may preferably releases the at least part of the breath of the subject under the influence of heat.

Furthermore, in accordance with yet more preferred embodiments of the present invention, in any of the systems described hereinabove, there may also be included an evacuated chamber in which the plurality of sample containers are located. In such a case, the sample containers should preferably be flexible bags.

Finally, in accordance with yet more preferred embodiments of the present invention, in any of the systems described hereinabove, the sample containers may have rigid walls and may preferably be evacuated before the commencement of the collection of the samples.

BRIEF DESCRIPTION OF THE DRAWINGS

The present invention will be understood and appreciated more fully from the following detailed description, taken in conjunction with the drawings in which.

DETAILED DESCRIPTION OF PREFERRED EMBODIMENTS

Figure 1:
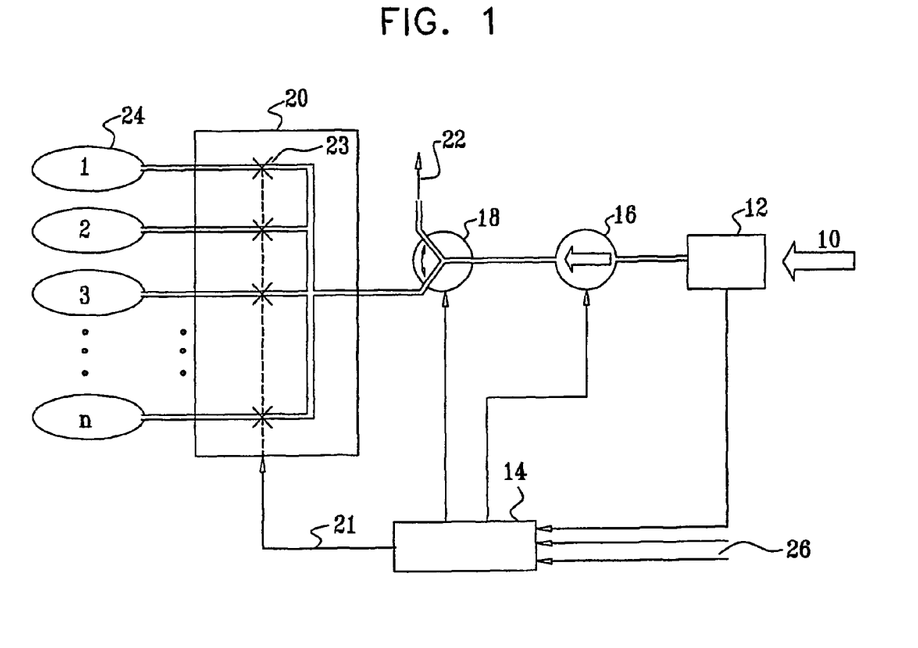
FIG. 1 is a schematic illustration of a breath collection system constructed and operative according to a first preferred embodiment of the present invention, for use with cannula breath collection.

Reference is now made to FIG. 1, which is a schematic illustration of a breath collection system constructed and operative according to a first preferred embodiment of the present invention. The subject's breath is collected at the breath collection port 10, preferably by means of an oral, a nasal or an oral/nasal cannula, as is known in the art, or by means of a breath tube into which the subject blows a breath. After entering the system, the breath sample passes into the breath sensor 12, which can be any one of a number of different types. According to one embodiment of the present invention, the breath sensor 10 incorporates a capnographic probe, operative to determine the carbon dioxide concentration in the breath as a function of time. An electronic signal proportional to the temporal carbon dioxide concentration of the breath is input to the system controller 14.

After exiting the breath sensor, the breath sample enters a pump 16. When a cannula is used to collect the breath, this pump ensures the inputting of the breath sample from the subject by means of its suction effect, and its continued motion through the rest of the system. In cases when a breathing tube is used for collecting the sample, the need for a pump is obviated.

After exiting the pump 16, the breath sample is preferably directed to a three way solenoid valve 18 whose flow position is controlled by means of a signal obtained from the system controller 14. The two alternate positions of the solenoid either pass the breath sample into the sample distributor unit 20, or discard the sample by ejecting it into the air 22. According to a first preferred embodiment, the controller 14 which provides the solenoid control signal, is programmed to determine when the subject's breaths are to be collected and when they are to be rejected, according to the predetermined test procedure, as described below.

According to a second preferred embodiment, the solenoid valve 18 is additionally or alternatively controlled so that only those parts of the breath samples are collected, where the carbon dioxide concentration is above a predefined level. Those parts where the carbon dioxide concentration is below that predefined level are rejected. Such a division can be derived from the output signal obtained from the capnographic breath sensor 12, and the controller can be adjusted to select or reject any predefined part of the breath waveform, according to the carbon dioxide level instantaneously detected. Further explanations and embodiments are to be found in the above-mentioned International Publication No. WO 99/14576. Alternatively and preferably, the solenoid valve 18 is controlled to collect only those parts of the breath where the carbon dioxide concentration is below a predefined level. Alternatively and preferably, the solenoid valve 18 is controlled to collect any predefined part of the waveform. According to further preferred embodiments of the present invention, the breath sensor need not specifically be a capnographic detector, but can be a detector of another gas such as oxygen, or ammonia, depending on the particulars of the test with which the breath collection system is to be used, or even a combination of a capnograph with another sensor. Furthermore, sensors of pressure, flow, acoustic noise, temperature and humidity may also preferably be used to detect breaths.

According to another preferred embodiment of the invention, the system collects samples in response to a signal related to an environmental effect, such as the presence of a hazardous gas in the air, as preferably detected by a hazardous gas detector.

The sample distributor 20 is operable to distribute separate breath samples or, according to the solenoid valve programming, parts of separate breath samples, to a number of individual sample containers 24. The timing of the distribution is determined by the controller 14. According to one preferred embodiment of the present invention, samples are collected at regular timed intervals, according to the predetermined requirements of the test. According to another preferred embodiment, samples are collected at times according to predetermined factors derived from signals input to the controller from physiological stimuli related either to the breaths themselves, such as, for instance, their end-tidal carbon dioxide content, or the breath rate, either of which would be obtained from the capnographic probe 12, or to physiological signals 26 other than those from the breaths themselves, some examples being the subject's pulse rate, breath flow rate, blood pressure, or temperature, as mentioned above.

According to yet more preferred embodiments of the present invention, the gas collection system could be activated by means of a signal generated by an implantable, introducible or ingestible medical device, such as a drug delivery system, a pH monitoring system, or by means of an endoscope or an endoscopic capsule probe. Thus, for instance, according to one preferred embodiment of these external activating signals, a drug dispensing pump can be used to dispense a therapeutic or a diagnostic drug at a designated point in the subject's body, and the dispensing time signal can be made to trigger breath test collection, such that the effectiveness of the drug can be verified by means of the breath test on the samples collected accordingly. Similarly, a signal can be provided by an endoscopic imaging capsule, such as that described in the article "Localization of a Wireless Capsule Endoscope in the G-I Tract" by D. Fischer et al, published in Gastro-Intestinal Endoscopy, Vol. 53, p. AB126 (2001). In such an application, the probe can be used to define the position of a test meal in the G-I tract, so that the breaths can be collected in correlation with the known position of the meal. Such an application can be advantageously utilized in performing the breath test for determining bacterial overgrowth. Likewise, a pH monitoring system could provide a signal to the system to collect a breath test sample or samples when the intragastric pH reaches a predetermined value.

The sample distributor 20 preferably comprises a multi-output solenoid valve, whose input can be switched to any of an array of output lines by means of electrical control signals, as is known in the art. Alternatively and preferably, an array of individual solenoid valves can be provided, connected together on the common input side and each feeding a separate output line to a single sample container. Each container is filled by opening its associated individual solenoid valve, until the required number of breaths to fill it is collected. The controller determines when the bag is full from a calculation performed using the known flow rate which is determined by the pump, the fluid resistance of the system, and the length and duration of the breaths. The valves can preferably be electro-mechanically or pneumatically operated.

The collection containers are preferably in the form of gas-tight bags, which are initially flat at the beginning of the test, and each of which is sequentially filled by the inflow of the breath sample directed to that container. The collection containers are preferably arranged in a separate unit, easily detachable from the rest of the breath collection system, such that once the required number of collection containers have been filled at the end of the collection period, this separate unit can be detached and taken to the gas analyzer system for analysis. Alternatively and preferably, each of the separate collection containers can be detached from the system and taken for analysis.

Figure 2A:
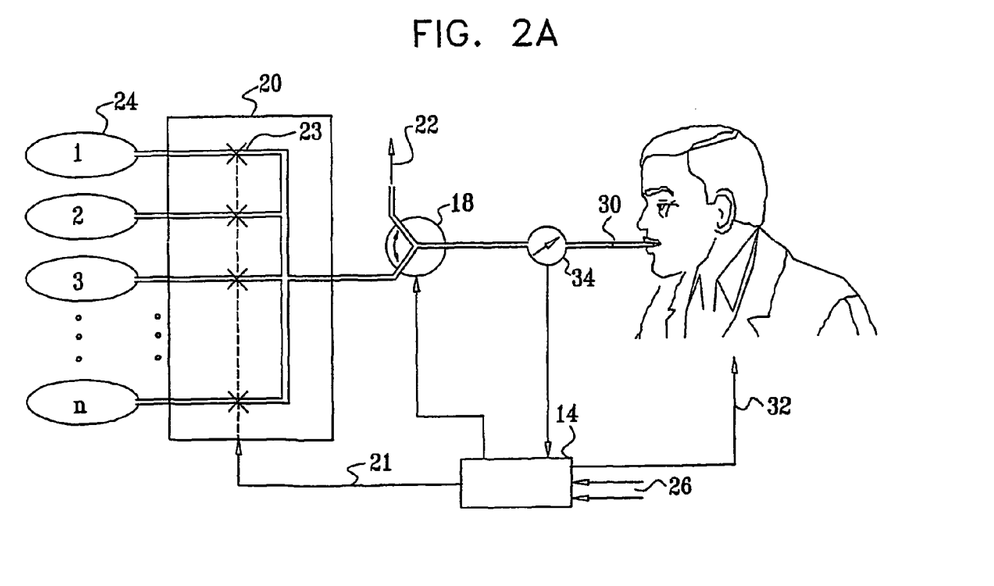
FIGS. 2A to 2C are schematic illustrations of breath collection systems constructed and operative according to other preferred embodiments of the present invention, and especially utilizable when the subject provides the samples by blowing into a breath tube, rather than using a cannula.
Figure 2B:
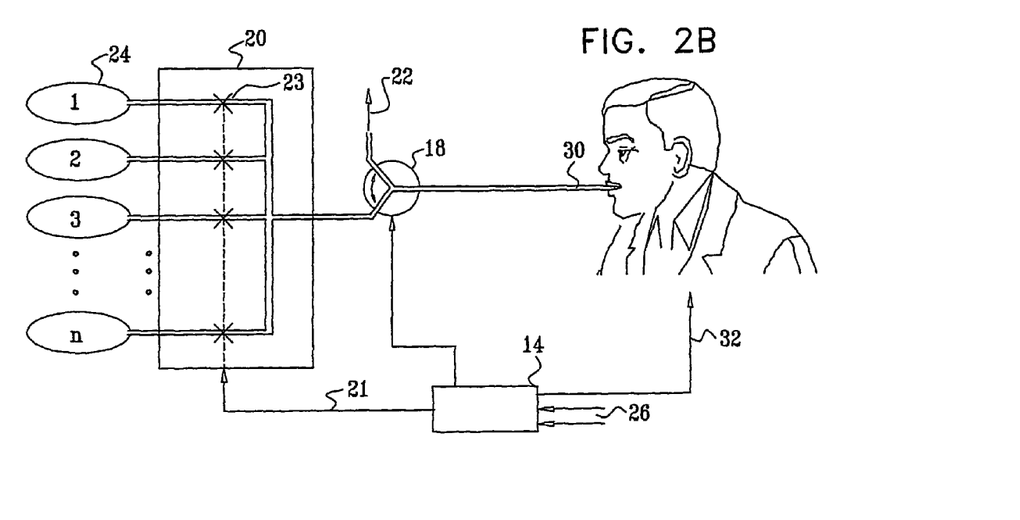
Figure 2C:
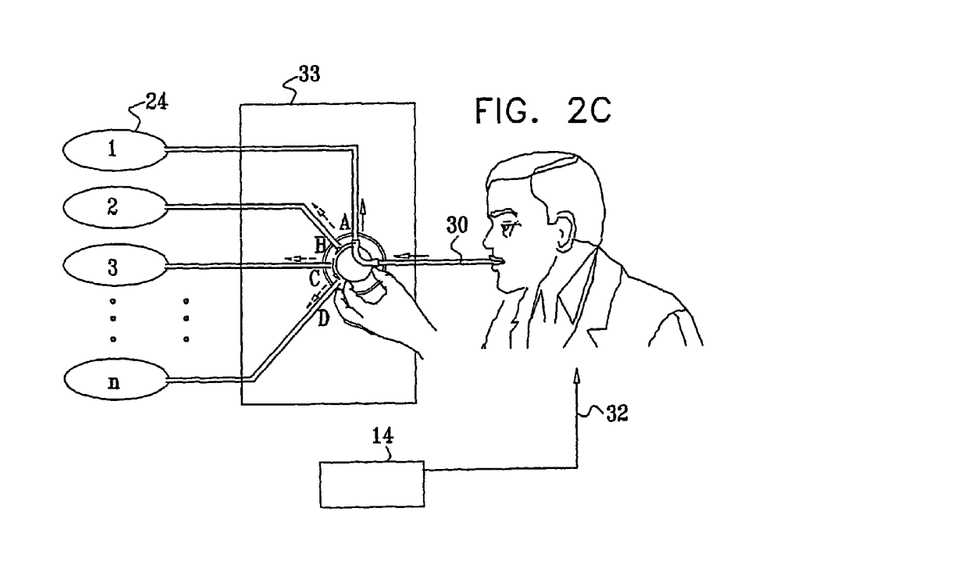

Reference is now made to FIGS. 2A to 2C, which are schematic illustrations of breath collection systems constructed and operative according to more preferred embodiments of the present invention. These embodiments differ from that shown in FIG. 1 in several respects. Firstly, sample collection from the subject is not performed independent of subject intervention by means of a nasal or nasal/oral cannula, but rather by means of a breath tube into which the subject actively blows 30. The subject is preferably prompted to provide the breath sample by means of a prompting signal 32, such as an aural tone, or a flashing light signal, provided at the correct time by the controller 14. This can either be at given time intervals predetermined according to the test being performed, or it could be in response to a physiological stimulus arising from another source 26, including a capnographic sensor, for use with breath tests where a specific physiological parameter value mandates that a breath sample be collected for testing.

Since the act of blowing a breath into the breath tube generates a positive pressure at the system input, according to these embodiments there is no need for a pump to collect and drive the breath samples through the system, as shown in the previous embodiment of FIG. 1. According to a first version of this embodiment, shown in FIG. 2A, the breath from the input tube is passed into a pressure sensor 34, whose output signal is processed by the controller 14, and which is operable to switch the solenoid valve 18 to collect or discard part of the breath sample. In this way, only those parts of breath samples are collected which arise from a pulmonary output pressure above a predetermined value. According to a second simpler version of this embodiment, shown in FIG. 2B, the input breath sample is passed directly to the sample distributor 20, where it is sent to its predetermined collection container, as described in the embodiment shown in FIG. 1. According to a third version, a capnography probe may detect the parts of the waveform of interest. In this third embodiment, there is no waveform comparable to that of the conventional nasal sampling case, but the capnographic probe can be used to accurately differentiate that part of the breath originating from dead space at the beginning of the subject's blowing, from the alveolar breath.

Since the embodiments shown in FIGS. 2A and 2B are dependent on the subject's co-operation in providing the breath sample when prompted, the system can be even further simplified, according to a further preferred embodiment of the invention, shown schematically in FIG. 2C, by having the subject also fulfil the distribution function. This can be done by providing a prompt 32 to the subject to switch from one sample container to the next as each breath sampling prompt is received from the controller 14, by means of a manually operated sample distributor 33. Alternatively, the subject can be prompted to switch to the next container after providing each breath sample or set of breath samples for each sample container. This embodiment thus simplifies the construction of the system by making the sample distributor manually operated 33.

Figure 3:
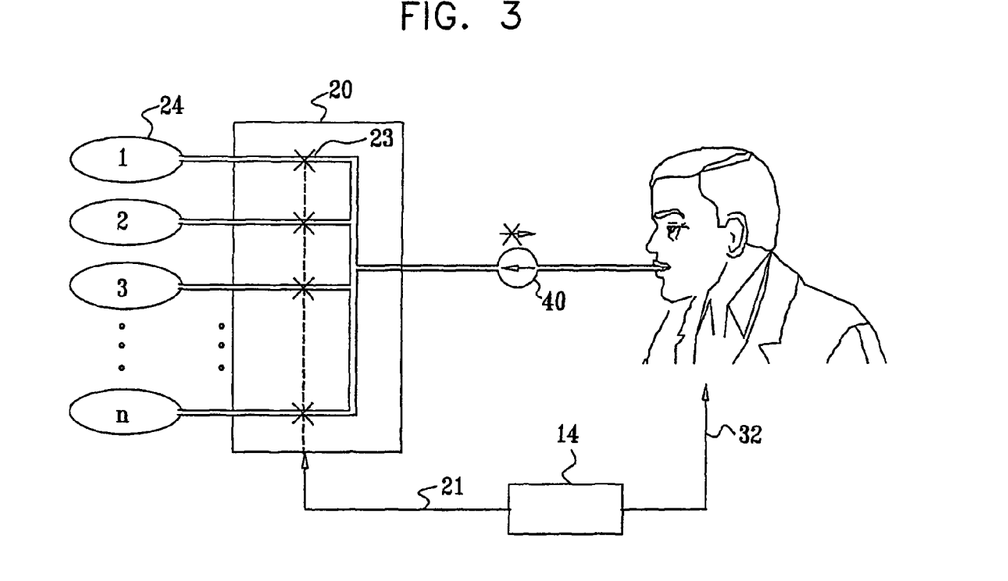
FIG. 3 is a schematic illustration of yet another preferred embodiment of the present invention, which is a simplified version of that shown in FIG. 2B using a check valve for directing the sample gas within the system.

Reference is now made to FIG. 3, which is a schematic illustration of a breath collection system constructed and operative according to yet another preferred embodiment of the present invention. This embodiment, like that shown in FIG. 2, utilizes a prompt signal to instruct the subject when the time has come to blow into the system to provide breath samples. However, the system is simpler than that shown in FIG. 2, in that essentially all of the breath blown out by the subject is passed to the sample distributor for collection by one or other of the sample containers. A one-way check valve 40, which opens at a certain predefined pressure, is provided to ensure that breath can only flow from the subject into the sample distributor, and not in reverse. This ensures the authenticity of the breath samples collected In the preferred embodiment shown in FIG. 3, distribution of the breaths to the different sample containers is controlled by the controller 14, as in previously described embodiments. In order to further simplify the system, the manually operated sample distributor 33 shown in FIG. 2C can also be advantageously used in this embodiment.

Figure 4:
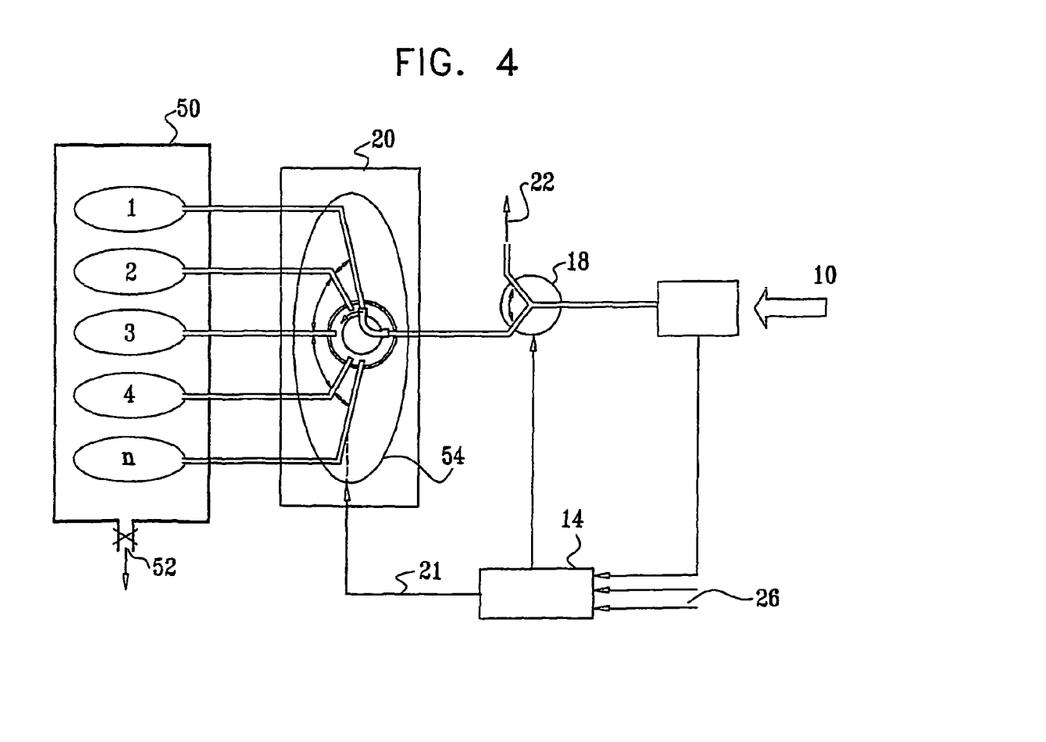
FIG. 4 is a schematic illustration of a breath collection system, constructed and operative according to yet another preferred embodiment of the present invention, in which the sample collection bags are contained in a vacuum chamber, thus obviating the need to provide a pump in the system.

Reference is now made to FIG. 4, which is a schematic illustration of a breath collection system, constructed and operative according to yet another preferred embodiment of the present invention. This embodiment is similar to that shown in FIG. 1, in that the use is made of a cannula to collect the breath and a breath sensor and solenoid valve to determine which part or parts of each breath to collect. However, in the embodiment of FIG. 4, there is shown a special embodiment of the collection container system, which obviates the need to provide a pump in the breath collection system. The collection containers 24 are all accommodated within a gas-tight outer chamber 50 which is preferably pumped to a vacuum before the start of the test. The presence of the vacuum ensures that when the solenoid valve and the sample distributor valve to a particular sample container bag are open, the container bag will fill up with a breath sample, or part of a breath sample, by drawing in the subject's breath from the cannula under the effect of the vacuum acting on the container bag's outer surface. Alternatively and preferably, use can be made of evacuated individual rigid containers, such as the commercially available Vacutainers®, connected directly to the distribution tubes of the sample distributor, which fill up under the influence of the vacuum within the containers.

In all of the above described embodiments of the present invention, it is important that the tubing from the exit of the solenoid valve 18 all the way to the sample container is as thin as possible, such that there is a minimal amount of residual gas in these tubes, relative to the volume of the collection container, before the commencement of the test. In this way, there is minimal dilution of the collected sample by this residual gas. In this connection, it is important to note that the current generally available Vacationers®, as used for blood collection, are not of sufficiently large volume to ensure this condition, and that this embodiment therefore requires the provision of rigid evacuated containers of sufficiently large volume.

Though each of the above-mentioned embodiments have been described as having specific features, it is to be understood that all of these features can be interchanged, where relevant, between the various embodiments, without departing from the scope of the present invention. Thus for example, it is to be understood that the use of a breath sensor, though only shown in the embodiments of FIGS. 1 and 4, could also be used in the embodiments of FIG. 2, though its advantage would be reduced when the subject provides the samples by blowing. Similarly, a manually operated sample distributor could be utilized in any of the embodiments shown.

Figure 5:
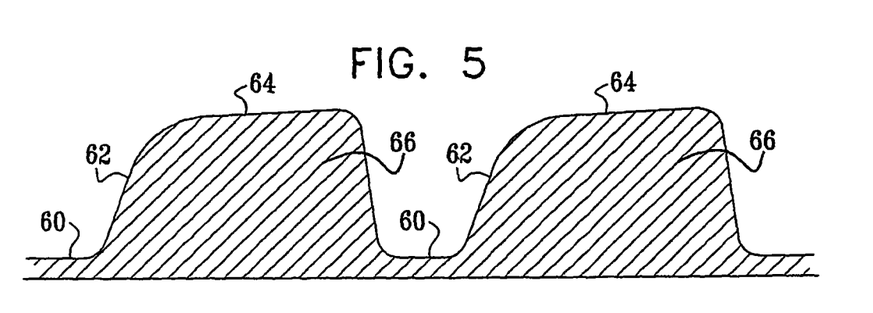
FIG. 5 is a schematic illustration showing how breath samples are separately defined for collection from different sections of the respiratory wavefront, and by means of the breath collection system of FIG. 1, are allocated to different collection containers.

Reference is now made to FIG. 5, which is a schematic representation of a breath waveform, showing the various parts of the waveform from which a capnographically controlled breath selector can select those parts required for a particular breath test analysis, especially for a VOC content breath collection. The breath sampled from the baseline region 60 of the waveform is generally representative of the air from the environment, since in this region, the subject is inhaling, and virtually none of the subject's pulmonary breath is mixed in. Breath or air from the subject's dead space is sampled from the rising part of the waveform 62, where the exhaled pulmonary breath pushes out the dead space gas, which is breath or air from the subject's mouth, trachea and bronchial tubes, which did not originate from the lungs themselves. Alveolar breath is collected generally from the plateau 64 of the waveform.

Furthermore, FIG. 5 can be used to illustrate another preferred embodiment of the present invention, wherein the carbon dioxide waveform is constantly analyzed to evaluate changes in the rate of carbon dioxide exhalation throughout the collection period, and to determine the total exhaled volume of carbon dioxide. Such methods for the determination of the total exhaled volume of carbon dioxide may be used advantageously, according to further preferred embodiments of the present invention, when performing breath tests of the type which require absolute knowledge of the volume of labeled molecules exhaled. Examples of such breath tests are those for determining liver function or pancreatic function. In such tests, a known number of labeled molecules of the substance to be metabolized is ingested by the patient, and the breath test must determine at various times during the test, the absolute number of such exhaled molecules resulting from the metabolic pathways through the organ being tested. The results of capnographic measurements provide the concentration of carbon dioxide in the subject's breath. Likewise, the breath test measurements generally provide the ratio of isotope concentrations in the breaths. In order to convert concentrations into the total volume of carbon dioxide exhaled during any period, the relationship between the results of the capnograph concentration measurements and the absolute breathed volume of carbon dioxide must be determined.

In other breath tests, it is not the absolute volume that is required to be determined, but the change in absolute volume as the test proceeds. Since the volume is not necessarily directly related to the concentration measured by the breath test, prior art breath tests do not always provide accurate results for such tests. Thus, for example, if the metabolic rate of the subject changes, the concentrations measured in the breath test may be unchanged, while the exhaled volume may have changed significantly.

According to presently accepted procedures, use is usually made of standard tables or expressions, known as the BSA calculations, to determine the exhaled carbon dioxide volume expected from the known weight and height of the subject. Such assumed volumes can be in error if the overall metabolic rate of the subject is abnormal because of other factors, such as illness, genetic or statistical variations. Furthermore, as mentioned above, changes in metabolic rate can occur because of temporary circumstances, and in such cases, the use of BSA expressions may result in inaccuracies. The exhaled volume of carbon dioxide are accurately measured in the prior art by means of specific carbon dioxide absorbing traps, or by calorimetric measurements, but such methods generally take time and are complicated to execute, in comparison with a simple breath test.

The above described methods and apparatus may be advantageously used, according to another preferred embodiment of the present invention, to estimate the absolute carbon dioxide exhaled volume at any time during the duration of the test, without unnecessarily complicating or significantly lengthening the breath test in progress. According to this preferred embodiment, the exhaled volume of carbon dioxide is measured for a short period by using one of the known accurate measurement devices or methods, such as a calorimeter, or an integrated flow measurement method. Once this base measurement has been obtained from the subject, the regular breath test is commenced, according to a first preferred embodiment, using a capnographic probe to provide waveform data such as is shown in FIG. 5. The area 66 under a series of waveforms is integrated over the period of the breath collection, and the total volume of carbon dioxide exhaled is assumed to be proportional to this integrated area. A constant carbon dioxide volume is indicative of a constant metabolic rate in the subject and the volume of carbon dioxide over any period is then assumed to be proportional to the integral under the waveform plot correlated with the absolute initial measurement of exhaled carbon dioxide volume performed at the start of the test. A constant volume of breath is thus assumed throughout the test. If the waveforms show a change in carbon dioxide concentration, then the assumed absolute carbon dioxide volume is adjusted according to the change in the concentration shown. The calibration of concentration against volume may be performed before the test, as described above, or at any time during or after the test.

Alternatively and preferably, the total carbon dioxide volume can be calculated by utilizing the initially measured absolute volume rate, and adjusting this rate according to other indicators of the general metabolic rate of the subject, such as the subject's pulse rate, or from measurement of the flow rate of the breaths, or more simply, from a measure of the pressure differential generated by this flow across a passage of known resistance to the fluid flow. However, for typical flow rates generated during breath tests on human subjects, it is found that the pressure differential which needs to be measured is of the order of only 2 mbar, such that although a pressure measurement is generally simpler to perform than a flow measurement, the very small magnitude of the pressure differential may complicate the measurement.

Furthermore, if it is the changes in exhaled volume that is the parameter of interest in the breath test, then according to other preferred embodiments of the present invention, the results of the breath test can be adjusted for changes in comparative exhaled volume according to any one, or a combination of more than one, of the above described indicators of metabolic rate, such as capnographically measured carbon dioxide integrated volume, or pulse rate, or blood pressure or breath flow rate.

Furthermore, the pulse rate can preferably be used to determine the correct or the most advantageous time to collect breath samples, since a steady pulse rate is indicative of the lack of interference to the subject's metabolism.

According to the above mentioned preferred embodiments of the present invention, any of the physiological inputs 26 shown in the above described embodiments in FIGS. 1 to 4, which have been previously described for use in determining the sampling rate or the tiring of the collection of breaths, can also be used as the above-mentioned indicators of the metabolic activity of the subject for correction of the assumed carbon dioxide volume, or for generally determining periods when, because of an atypical metabolic state, collection of the breaths is nor desirable. This metabolic indicator can also be the capnographic probe 12 output itself, which provides information about the metabolic state of the subject. According to these preferred embodiments, metabolic indications from any of these inputs can also be used to apply a correction factor for implied volume change to the information processed by the instrument which analyses the collected gases.

Figure 6A:
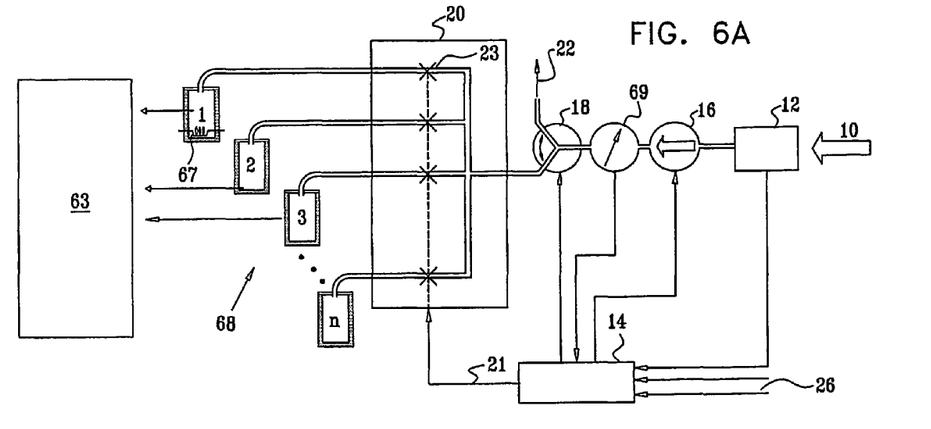
FIGS. 6A and 6B are schematic illustrations of breath collection systems, and a breath VOC analyzer, constructed and operative according to yet further preferred embodiments of the present invention, in which the sample collection bags shown in the systems of the above drawings are replaced by adsorbent traps such as for absorbing the VOC content of the breath.

Reference is now made to FIG. 6A, which is a schematic illustration of a system according to another preferred embodiment of the present invention, in which the sample collection bags are replaced by absorbent traps for collecting VOC's or the specific gas intended to be measured The components of this system in FIG. 6A have been given the same reference characters as those of the previous embodiments of FIGS. 1 to 4. For VOC measurements, such traps could preferably contain activated charcoal, carbon black, molecular sieves, polymers, or any other suitable VOC absorbing material. For isotopic carbon dioxide measurements, soda lime or lithium hydroxide could preferably be used. Such absorbing materials are characterized by absorbing the specified compound at room temperature and releasing it while heated to temperatures of between 100° C. and 450° C., according to the material. The volumes of collected gas samples are preferably measured by means of a flow meter 69 or similar device, as described above, and the flow levels are preferably used by the controller 14 to ensure that an equal volume of gas is directed to each container. As an alternative, the flow levels may be recorded for further analysis together with the carbon dioxide concentrations obtained from the capnographic probe.

Figure 6B:
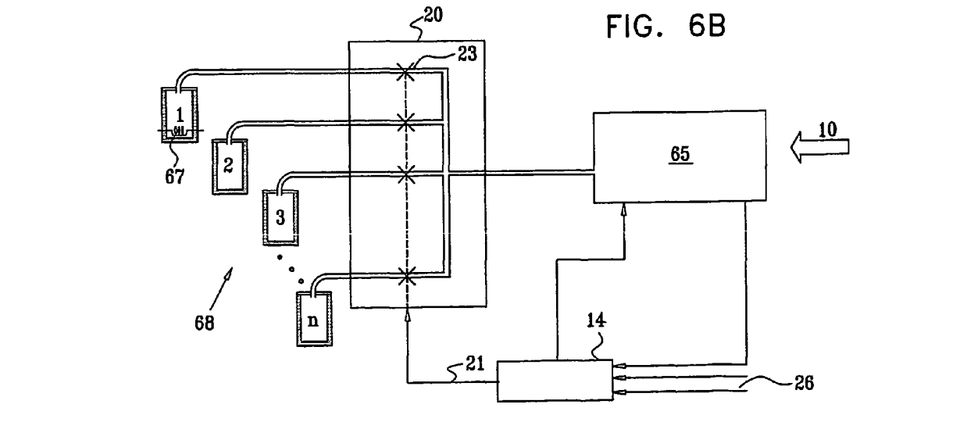

Alternatively and preferably, the volumes of gas to be delivered to the absorption traps, could be measured by accumulating given volumes of gas by means of an intermediate chamber 65, which preferably has a capnographic probe 12 at its input, as is known in the art. This enables equal volumes of gas to be passed to the absorption traps, so that the volumes of gas trapped are normalized to each other. Such a system utilizing an intermediate chamber system 65 is schematically illustrated in FIG. 6B. The intermediate chamber system 65 is preferably coupled to or comprises a capnographic probe or breath sensor 12 and thus forms a system that comprises all of the breath monitoring and control functions, which select the predetermined part or parts of the breath waveform and accumulate those parts until the desired volume is achieved, such that the controller 14 has only to ensure that each successive accumulated volume from the intermediate chamber system is passed to a successive collection container. The carbon dioxide concentration of each sample can be recorded for further analysis if required.

The absorption traps can be heated to release the absorbed gases for measurement A heating device, such as a resistor, could preferably be included in the sample container, and connected to an external power source, such that the gas contained in each trap is selectively and sequentially released by means of activation of the heater and the solenoid valves. Alternatively this gas collection and release system could provided as an accessory for use with other gas collection systems, or can be implemented using standard laboratory equipment as described in the prior art. The samples are transferred to a VOC analyzer 63, such as is known in the art, for analysis of the VOC concentration in each sample. Gas measurement of VOC concentrations can preferably be performed by subtracting the concentration of VOC found in the ambient air from that found in the alveolar air, as described, for instance, in the above-mentioned articles by J. D. Pleil et al., and by Wu-Hsun Cheng et al.

Although the measurement of VOC has been described in relation to the embodiment of FIGS. 6A and 6B, using absorbent traps as collection containers, this being a simple method of collecting VOC's, it is to be understood that the apparatus is not meant to be limited to such containers, but can also be performed with the systems described in any of the other embodiments of the present invention, subject to the VOC concentration being extractable from that container and being measurable therefrom.

Figure 7A:
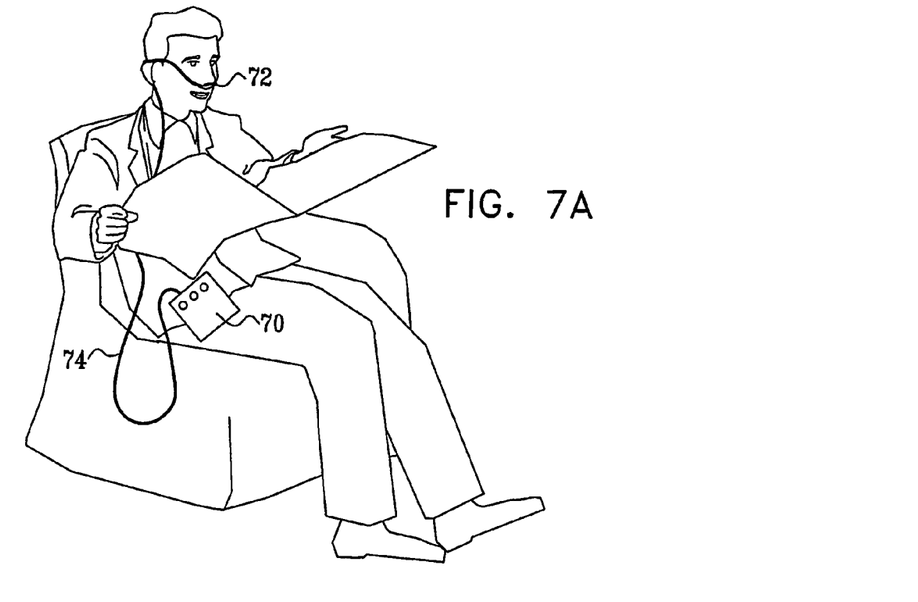
FIGS. 7A and 7B are schematic illustrations of a subject wearing a complete breath collection system as shown schematically in FIG. 1, according to two different additional preferred embodiments of the present invention.
Figure 7B:
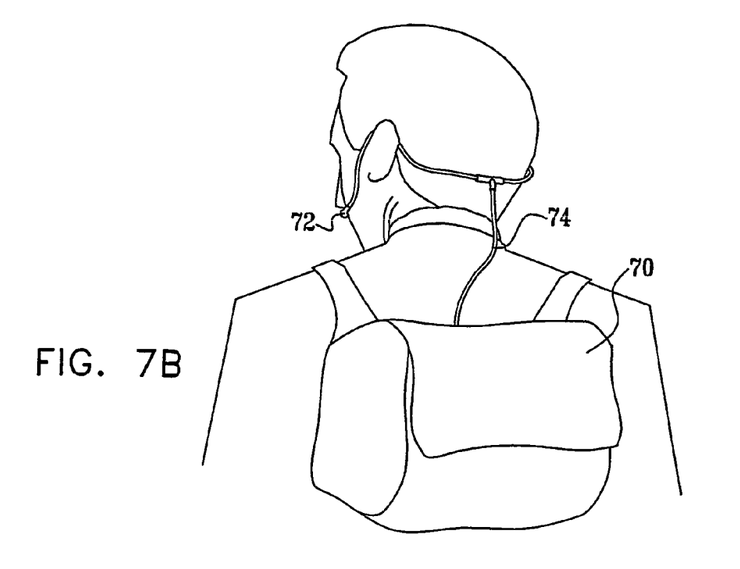

Reference is now made to FIGS. 7A and 7B, which schematically illustrate a subject using a portable breath collection system 70 according to further preferred embodiments of the breath collection systems shown previously. Such portable embodiments are easily carried by the subject, for example on the subject's belt as shown in FIG. 7A, or in a back-pack, as shown in FIG. 7B, or in a small hand-carried bag.

The breath samples are preferably collected from the subject in the conventional manner by means of a nasal cannula 72, and are conveyed to the collection system 70 by means of a thin cannula tube 74. These embodiments thus enable the subject to continue the performance of the breath test, even for long periods of time, while carrying on his/her regular routine. In this respect, these preferred embodiments of the present invention may be regarded as being the capnographic equivalents of the well-known Holter monitors used for monitoring cardiac activity while the subject is carrying on his regular routine.

As mentioned above, metabolic indicators as obtained by the user's pulse rate, blood pressure or the capnographic probe itself, or by any other useful indicator, can preferably be used to correct the assumed volume of carbon dioxide exhaled, as explained hereinabove, or to instruct the portable breath collection system to stop collecting temporarily, or to "label" some of the collection containers with the metabolic state of the subject existent at the time the breaths in that container were collected, so that an appropriate correction can be applied to the analysis of the container when ultimately performed.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A portable system for collecting a plurality of samples of breath of a subject, the system comprising:
    a nasal cannula adapted to convey exhaled breaths from the subject to said system;

a pump for collecting said breaths from the nasal cannula of the subject by means of the pump's suction effect, ensuring the inputting of the breath sample; said pump located in the system at a position post said cannula and post a capnographic analyzer and before a plurality of sample containers;

said plurality of sample containers;

said capnographic analyzer adapted to indicate the waveform of said exhaled breaths of the subject;

a controller adapted to receive input at least from said capnographic analyzer;

a sample distributor adapted to receive said breath motioned by said pump and to direct different predetermined samples of said exhaled breaths to different ones of said plurality of sample containers, according to said controller; and a valving system adapted to select at least part of said exhaled breaths for passing to said sample distributor, according to said controller.

2. A system according to claim 1, wherein said controller is further adapted to cause said valving system to select said at least part of said breaths according to at least one characteristic of said breath selected from the group consisting of the carbon dioxide concentration, the oxygen concentration, the excess pressure, the temperature, the humidity, the flow rate and the sound of said breaths.

3. A system according to claim 2, wherein said at least part of said breaths is determined by said carbon dioxide concentration.

4. A system according to claim 3 wherein said at least part of said breath is selected for passing to said sample distributor when said carbon dioxide concentration of said breath is at the plateau value of its waveform, such that alveolar air is sampled.

5. A system according to claim 3, wherein said sample distributor is adapted to direct breath exhaled when said carbon dioxide concentration of said breath is at the plateau value of its waveform into a first one of said sample containers, and breath inhaled when said carbon dioxide concentration of said breath is at the baseline of its waveform into a second one of said sample containers.

6. A system according to claim 1, wherein at least one of said plurality of sample containers contains a material which absorbs a predetermined gas of said breath of the subject.

7. A system according to claim 6, wherein said at least one of said plurality of sample containers comprise a heater for expelling said predetermined gas of said breath of the subject.

8. A system according to claim 1, wherein at least one of said sample containers is a flexible bag.

9. A system according to claim 1, wherein at least one of said sample containers has rigid walls and is evacuated before collection of said breaths.

10. A system according to claim 1, wherein said predetermined samples of said exhaled breaths contain a volatile organic compound.

11. A system according to claim 1 wherein said controller is further adapted to cause said valving system to select said at least part of said breath according to at least one characteristic of the subject selected from the group consisting of the subject's breath composition, breath rate, heart rate, blood pressure, gastric pH value and temperature.

12. A system according to claim 1 and wherein at least one of said sample containers is a flexible bag.

13. A system according to claim 1 and wherein at least one of said sample containers has rigid walls and is evacuated before collection of said samples.

14. A system according to claim 1 and wherein said samples are adapted to be analyzed in one or more breath tests.

15. A system according to claim 14 and wherein said one or more breath tests comprise: determining effectiveness of a drug, determining bacterial overgrowth, determining volatile organic compounds (VOC) content, determining a volume of a labeled molecule exhaled, determining ratio of isotope concentrations, determining liver function, determining pancreatic function or any combination thereof.

* * * * *

UNITED STATES PATENT AND TRADEMARK OFFICE
CERTIFICATE OF CORRECTION

PATENT NO. : 8,485,984 B2  
APPLICATION NO. : 10/506872  
DATED : July 16, 2013  
INVENTOR(S) : Giron et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1,156 days.

Signed and Sealed this  
Twenty-sixth Day of November, 2013

Margaret A. Focarino  
*Commissioner for Patents of the United States Patent and Trademark Office*